United States Patent [19]

Shepro et al.

[11] Patent Number: 5,278,143

[45] Date of Patent: Jan. 11, 1994

[54] PROPHYLACTIC AND THERAPEUTIC METHODS FOR TREATING INTERLEUKIN-MEDIATED EDEMAS

[75] Inventors: David Shepro, Boston, Mass.; J. Steven Alexander, Nashville, Tenn.

[73] Assignee: Trustees of Boston University, Boston, Mass.

[21] Appl. No.: 807,668

[22] Filed: Dec. 16, 1991

Related U.S. Application Data

[63] Continuation of Ser. No. 416,905, Oct. 4, 1989, abandoned, which is a continuation-in-part of Ser. No. 417,121, Oct. 4, 1989, abandoned, and a continuation-in-part of Ser. No. 185,650, Apr. 25, 1988, abandoned.

[51] Int. Cl.$^5$ .......................... A61K 37/02; C07K 7/64
[52] U.S. Cl. .......................................... 514/11; 514/9; 514/870; 514/922; 530/317; 530/321; 424/85.2
[58] Field of Search .................... 530/317, 321; 514/9, 514/11, 870, 922; 424/85.2

[56] References Cited

U.S. PATENT DOCUMENTS 4,690,915  9/1987  Rosenberg ............................. 514/2

OTHER PUBLICATIONS

Rudinger, Peptide Hormones, Parsons (Ed.) U. Park Press, Baltimore, pp. 1–7 (1976).
Doukas et al., Blood, vol. 69, No. 6 pp. 1563–1569 (Jun. 1987).
Frimmer, Chem. Abstracts, vol. 71, No. 99937m (1969).
Wieland et al., Crit. Rev. Biochem. vol. 5, pp. 185–260 (1978).
Welbourn et al., *J. Appl. Physiol.* 70: 1364–1368 (1991).

*Primary Examiner*—Y. Christina Chan
*Attorney, Agent, or Firm*—David Prashker

[57] ABSTRACT

Unique methods for treating interleukin-mediated edemas in living subjects are provided comprising administering an effective amount of a composition selected from the group consisting of phallotoxins, phallotoxin analogues, antamanide, or an antamanide analogue to the subject. The methods offer prophylactic and therapeutic modes of treatment for both localized and systemic interleukin-mediated edemas. The compositions of choice may be applied topically or given parenterally; and may be employed with other diverse agents for treatment of both inflammatory and non-inflammatory edemas.

7 Claims, 3 Drawing Sheets

PROPHYLACTIC AND THERAPEUTIC METHODS FOR TREATING INTERLEUKIN-MEDIATED EDEMAS

GOVERNMENTAL SUPPORT

Research support for the present invention was provided by a grant from the Community Technology Foundation of Boston, University.

This application is a continuation of application Ser. No. 416,905, filed Oct. 4, 1989, now abandoned; which is a continuation-in-part of U.S. patent application Ser. No. 185,650 filed Apr. 25, 1988 now abandoned; and a continuation-in-part of copending U.S. patent application Ser. No. 417,121, filed Oct. 4, 1989, now abandoned.

FIELD OF THE INVENTION

The present invention is concerned with inflammatory and non-inflammatory (hydraulic) associated edemas and is particularly directed to prophylactic and therapeutic methods for treating localized and systemic edemas caused or mediated by interleukins.

BACKGROUND OF THE INVENTION

Edema is the term generally used to describe the accumulation of excess fluid in the intercellular (interstitial) tissue spaces or body cavities. Edema may occur as a localized phenomenon such as the swelling of a leg when the venous outflow is obstructed; or it may be systemic as in congestive heart failure or renal failure. When edema is severe and generalized, there is diffuse swelling of all tissues and organs in the body and particularly pronounced areas are given their own individual names. For example, collection of edema in the peritoneal cavity is known as "ascites"; accumulations of fluid in the pleural cavity are termed "hydrothorax"; and edema of the pericardial sac is termed "pericardial effusion" or "hydropericardium". Non-inflammatory edema fluid such as accumulates in heart failure and renal disease is protein poor and referred to as a "transudate". In contrast, inflammatory edema related to increased endothelial permeability is protein rich and is caused by the escape of plasma proteins (principally albumin) and polymorphonuclear leukocytes (hereinafter "PMNs") to form an exudate.

Edema, whether inflammatory or non-inflammatory in nature, is thus an abnormality in the fluid balance within the microcirculation which includes the small arterioles, capillaries, and post-capillary venules of the circulatory system. Normal fluid balance and exchange is critically dependent on the presence of an intact and metabolically active endothelium within the vasculature. Normal endothelium is a thin, squamous epitbelium adapted to permit free, rapid exchange of water and small molecules between plasma and interstitium; but one which limits the passage of plasma proteins with increases in protein size.

The endothelial lining of all arterioles and venules, and most capillaries in the body, is of the continuous type, having an unbroken cytoplasmic layer with closely apposed intercellular junctions. Physiological studies [Renkin, E., *Circ. Res.* 41:735–743 (1977); Renkin, E., *ACTA Physiol. Scand. (Suppl.)* 463:81 (1979); Bottaro et al., *Microvasc. Res.* 32:389–398 (1986)] have demonstrated normal endothelial permeability for water and small molecules by the existence of water-filled small pores approximately 6 nanometers (hereinafter "nm") in radius or by slits about 8 nm wide. There is also believed to be a system of larger sized pores about 25 nm in radius which accounts for the small quantities of protein and other large solutes that normally cross the endothelial wall barrier.

A variety of different disturbances can induce a condition of edema. These include: an elevated venous hydrostatic pressure which may be caused by thrombosis of a vein or any other venous obstruction; hypoproteinemia with reduced plasma oncotic pressure resulting from either inadequate synthesis or increased loss of albumin; increased osmotic pressure of the interstitial fluid due to abnormal accumulation of sodium in the body because renal excretion of sodium cannot keep pace with the intake; failure of the lymphatics to remove fluid and protein adequately from the interstitial space; an increased capillary permeabiity to fluids and proteins as occurs in the inflammatory response to tissue injury; an increased mucopolysaccharide content within the interstitial spaces; and an iatrogennic induced or mediated increase or accumulation of fluid and protein resulting from the administration of a pharmacologically active lymphokine during the course of treatment by a physician or surgeon. This last-identified disturbance merits a more detailed examination in view of recent developments in immunotherapy.

Lymphokines comprise a broad class of biologically active substances which are secreted by various types of lymphocytes in-vivo and in-vitro, especially by different populations of T-cell lymphocytes. Perhaps the most controversial presently is the family of interleukins, which presently comprises: Interleukin-1 ("IL-1") involved in the activation of resting T-cells; Interleukin-2 ("IL-2") which mediates the proliferation of T-cells and induces cytotoxic activity in T-cells; Interleukin-3 ("IL-3") which causes the proliferation of mast cells and granulocytes; Interleukin-4 ("IL-4") which mediates the proliferation, activation, and differentiation of B-cells, T-cells, and natural killer cells; and Interleukin-6 ("IL-6") which induces the growth and differentiation of B-cells and T-cells [Spits et al., *J. Immunol.* 139:1142 (1987); Kawakami et al., *J. Exp. Med.* 168:2183 (1988); Spits et al., *J. Immunol.* 141:29 (1988); and Tartakovsky et al., *J. Immunol.* 141:3863 (1983)].

Of particular interest is Interleukin-2 ("IL-2") and its analogues whose isolation, chemical formulation and structure, and synthesis by conventional wet chemistries and by recombinant DNA techniques have been intensively pursued [see for example U.S. Pat. Nos. 4,490,289; 4,138,927; 4,569,790; 4,578,335; 4,761,375; 4,518,584; 4,604,377; 4,564,593; and the references cited therein]. The use of Interleukin-2 as a therapeutic composition has followed two very different approaches. The first line of development is exemplified by the IL-2 immunotherapy technique for treating cancers originated by Dr. Steven A. Rosenberg [Rosenberg, S. A., *Immuno. Today* 9:58–62 (1988) and the references cited therein]. That approach involves the removal of lymphoid cells from a tumor-bearing host; an in-vitro expansion of the host's cells by culture in Interleukin-2 containing culture media to produce lymphokine-activated killer ("LAK") cells; and a re-introduction of the LAK cell culture into the living host accompanied by successive administrations of IL-2 directly to the tumor-bearing host. This approach has been termed "adoptive immunotherapy." A variation of this development is the use of IL-2 directly as an anti-cancer agent. This is exemplified by Patent Nos. WO-8600334 published 860116; JP-60185721 published 850921; U.S. Pat. No. 4,645,830; EP-145390 published 850619; and WO8500606 published 850214.

The second general approach has been to chemically link the Interleukin-2 molecule to another ligand having known biological properties to form a hybrid. The IL-2 portion of the hybrid serves a specific binding protein able to selectively bind to IL-2 receptor sites on the surface of living cells; the IL-2 portion of the hybrid thus served as the means of delivering and selectively introducing the other component of the hybrid into a chosen cell population having IL-2 receptor sites on their cell surface. This second approach is exemplified by: U.S. Pat. Nos. 4,675,382 and 4,745,180; GB-2189393 published 871028; EP-269455 published 88060; EP-256714 published 880224; and EP236987 published 870916.

A major problem and deficiency for the in-vivo use of interleukins generally and of IL-2 in particular has been the now well recognized phenomenon of uncontrolled edema as a concomitant side-effect of interleukin administration. The observation of massive edema locally and systemically has been termed "vacular leakage syndrome" and is now seen as a regular and unavoidable consequence of using interleukins therapeutically in either uncoupled or complexed/hybridized form. Representative publications describing the uncontrolled edemas caused or mediated by the administration of an interleukin include: Carlsen, E. and H. Prydz, *Thrombosis and Harmostasis* 58:257 (1987); Giddings, J. C. and L. Shall, *Thrombosis and Haemostasis* 58:31 (1987); Kotasek et al., *Clin. Res.* 35:660A (1987); Ellison et al., *Anat. Rec.* 218:41A (1987); and the references cited therein]. In so far as is presently known, there is no effective composition or method to meaningfully control, reduce, or substantially eliminate the resulting vascular leakages and the massive edemas caused and/or mediated by the in-vivo administration of an interleukin for any therapeutic purpose. Furthermore, there is presently no effective agent or admixture of substances useful as a prophylactic against an interleukin-mediated edema.

Remote from and completely unrelated to these investigations of interleukins were other research efforts directed towards the isolation and identification of the component substances of the poisonous green fungus *Amanita phalloides*, known as the "green death cap" or "deadly agaric" mushroom [Lynen and Wieland, *Justus Liebigs. Ann. Chem.* 533:93–117 (1938); Wieland and Schnabel, *Justus Liebigs Ann. Chem.* 657: (1962)]. At least ten peptide-like substances of complex structure have been identified; most of these substances have proven to be extremely toxic liver toxins [*Liebig's Ann. Chem.*, volume 617, page 152, 1958; *Pharmacol. Reviews*, volume 7, page 87, 1959; *Liebig's Ann. Chem.*, volume 704, page 226, 1967]. Upon isolation and empirical analysis of the naturally occurring individual components of *Amanita phalloides*, however, investigators found at least two different naturally occurring classes of chemical compositions: phallotoxins and antamanide.

The class of phallotoxins as a whole is best exemplified by the substance known as phalloidin, one of seven naturally occurring member toxins forming the class. Phalloidin is very rapid in action. High dose levels given intramuscularly cause death of mice or rats within one or two hours. The $LD_{50}$ dose in albino mice is only 3.3 micrograms per gram of body weight given intramuscularly. Phalloidin acts by binding actin, a cytoskeletal protein [Russo et al. *Am. J. Pathol.* 109:133 (1982)]. Reviews of the chemical structure and toxicology of all toxins derivable from *Amanita phalloides* including phalloidin have been reported in the literature [Wieland and Wieland, *Pharmacol. Rev.* 11:87–107 (1959); Wieland, T., *Fortschr. Chem. Org. Naturst.* 25:214–250 (1967); Faulstich H. and T. Wieland, *Eur. J. Biochem.* 22:79 (1971); Wieland and Faulstich, *Crit. Rev. Biochem.* 5:185–260 (1978)].

Sporadically, some investigators have employed phalloidin within in-vitro experiments for its effects upon living cells. For example, the interaction of phalloidin with actin was one of the earliest reported demonstrations [Lengsfeld, A. M., *Proc. Natl. Acad. Sci. USA* 71:2803–2807 (1974)]. Subsequently, it was shown that phalloidin treatment induces changes in the intercellular junctions of rat hepatocytes [Montsano et al., *J. Cell. Biol.* 67:310–319 (1975)]. More recently, phalloidin was employed to increase the resistance of Necturus gallbladder epithelium to the passage of an electrical current [Bentzel et al., *Amer. J. Physiol.* 239:C75–C89 (1980)]. The use of phalloidin in such investigative studies has therefore been primarily as a research tool by which to further characterize and elucidate the mechanism of cytoskeleton action within living cells.

The other major class was identified and founded based on the one naturally occurring substance, antamanide, which was not only completely non-toxic of itself; but also was found capable of actually annulling the toxic effects of fatal doses of phalloidin and/or of protecting the liver completely when administered in therapeutic doses [Wieland et al., *Angew. Chem.* 80:208 (1968)]. Subsequent investigations of this cyclic decapeptide, antamanide, then proceeded in two different directions: one research effort involved methods of synthesizing, purifying, and preparing analogues of antamanide. These investigations are examplified by: U.S. Pat. Nos. 3,705,887 and 3,793,304; Anderson et al., *J. Am. Chem. Soc.* 88:1338–1339 (1966); Anderson et al., *J. Am. Chem. Soc.* 89:5012–5017 (1967); Wieland, T., *Angew. Chem.* (Internat. Edit.) 7:204–208 (1968); Ovchinnikov et al., *Proc. Eur. Pept. Synp.* 11:403–415 (1973); Wieland et al., *Liebig's Ann. Chem.*, number 3, pages 371–380, 1977; Burgermeister et al., *Eur. J. Biochem.* 44:305–310 (1974); Tonelli, A. E., *Biochemistry* 12:689–692 (1973); Patel, D. J., *Biochemistry* 12:677–688 (1973); Ivanov et al., *Biochem. Biophys. Res. Comm.* 42:654–663 (1971); and Bir et al., *J. Peptide Protein Res.* 13:287–295 (1979)].

In comparison, the other investigations focused upon the physiological and pharmacological attributes of naturally occurring antamanide and its synthetic analogues. These investigations are exemplified by the following: Faulstich et al., *Hoppe Scylers. Z. Physiol. Chem.* 359:1162–1163 (1974); Ovchennikov et al., *Experientia* 28:399–401 (1972); Wieland et al., *Proc. Nat. Acad. Sci. U.S.A.* 81:5232–5236 (1984); Carle, I. L., *Proc. Nat. Acad. Sci. U.S.A.* 82:7155–7159 (1985); Munter, K. D. and H. Faulstich, *Biochim. Biophys. Acta* 860:91–98 (1986); Nielsen, O., *Acta Pharmacol. Toxicol.* 59:249–251 (1986); and Raymond et al., *Eur. J. Pharmacol.* 138:21–27 (1987).

In all of these published investigations and reports, the cyclic decapeptides comprising antamanide and its analogues were recognized solely as chemical agents capable at very low dosage of counteracting the effects of an absolutely fatal dose of phalloidin or of completely protecting the liver against such a fatal dose of phalloidin. Only recently was there any investigation into areas concerning cell proliferation and wound healing [Choi et al., FASEB J. 3:A290, Abstract No. 368 (1989)]. This Abstract was the first publication to suggest that antamanide might serve as a therapeutic agent in the treatment of vascular disease.

Accordingly, the use of antamanide and the synthetic analogues remains primarily and predominantly as an anti-toxin against the effects of phalloidin; and phallotoxins as a class are known primarily for their toxic effects and, therefore, used primarily as a research tool. There is, thus, no known relationship for these substances with respect to controlling interleukin-mediated edemas in-vivo.

SUMMARY OF THE INVENTION

The present invention provides methods for therapeutically or prophylactically treating interleukin-mediated edema in a living subject. The method for therapeutically treating interleukin-mediated edema comprises the step of administering an effective amount of a substance selected from the group consisting of phallotoxins, phallotoxin analogues, antamanide, or an antamanide analogue to the subject after occurrence of the edema. The method for prophylactically treating interleukin-mediated edema comprises the step of administering an effective amount of a phallotoxin, a phallotoxin analogue, antamanide, or an antamanide analogue to the subject prior to the occurrence of an interleukin-mediated edema. Either methodology inhibits the permeability of fluid, macromolecules, and blood cells across the microvasculature thereby acting directly on the clinical manifestations of the edema and avoiding indirect metabolic cascades and pathways.

The prophylactic methodology can be employed in settings where iatrogenic-induced edema typically occurs such as with the use of adoptive immunotherapy or the use of interleukin-containing hybrids. The therapeutic methodology can be used to attenuate both an inflammatory response as well as a non-inflammatory reaction current with the in-vivo administration of an interleukin. Moreover, the antamanides, antamanide analogues, phallotoxins, and phallotoxin analogues may be used alone or in combination with other substances known to affect cellular metabolic pathways.

BRIEF DESCRIPTION OF THE FIGURES

The present invention may be more easily and completely understood when taken in conjunction with the accompanying drawing, in which.

DETAILED DESCRIPTION OF THE PREFERRED EMBODIMENTS

Figure 1:
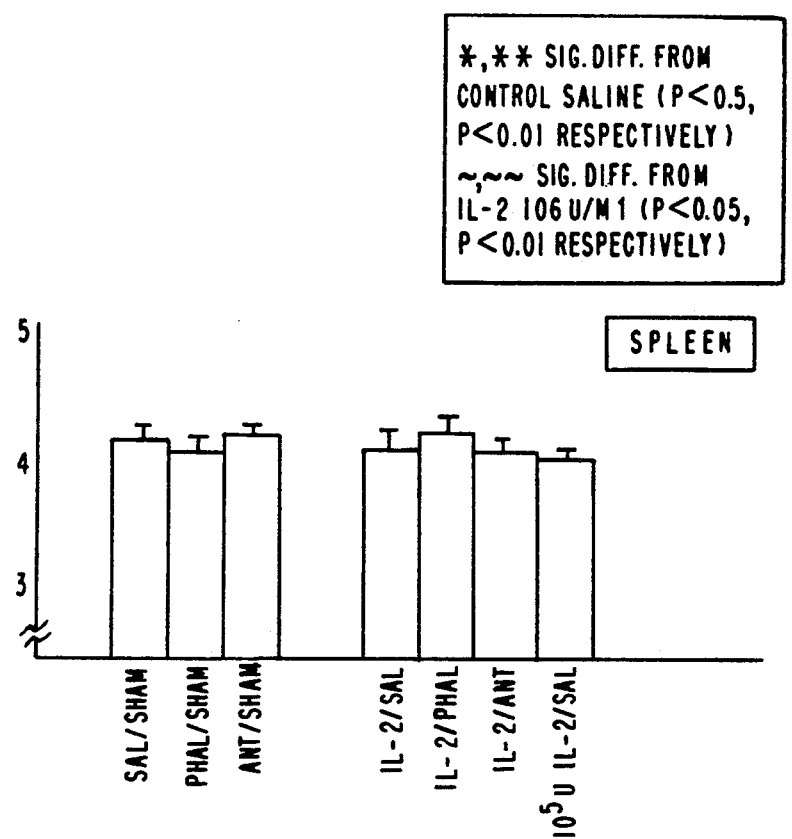
FIG. 1 is a graph illustrating the spleen wet to dry weight ratios after in-vivo administration of Interleukin-2, phalloidin, and antamanide alone and in combination.

The present invention is the general methodology for prophylactically or therapeutically treating localized or systemic interleukin-mediated or induced edemas in a living subject which comprises the step of administering an effective amount of an antamanide, or an antamanide analogue, or a phallotoxin, or a phallotoxin analogue to the living subject either before or after ocurrence of the interleukin-mediated edema in the subject. The broadest chemical definition of the class of compositions comprising antamanides and its analogues is provided by Formula I below:

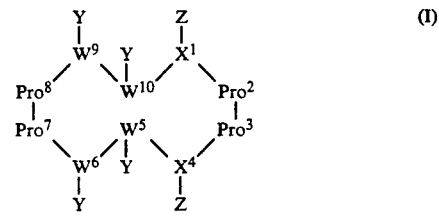

(I)

wherein W individually is an amino acid having at least one ring structure comprised of not more than 6 carbon atoms;

X individually is an acyclic amino acid comprised of 3–9 carbon atoms;

Y individually may be omitted entirely, but when present is selected from the group consisting of hydrogen, a hydroxyl group, a halogen, a hydrocarbon, and a substituted hydrocarbon; and Z individually may be omitted entirely, but when present is selected from the group consisting of hydrogen, a halogen, a hydrocarbon, and a substituted hydrocarbon.

A preferred broad definition of the cyclic decapeptide compositions and structures comprising the class of antamanides and antamanide analogues is given by Formula II below:

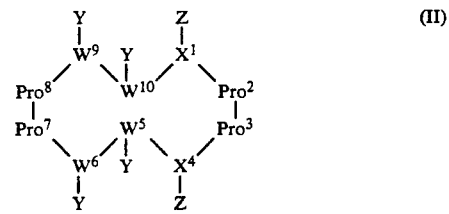

(II)

wherein W individually is an amino acid having a benzene ring in its structure;

X individually is an amino acid selected from the group consisting of valine, alanine, leucine, and isoleucine;

Y individually may be omitted entirely, but when present is selected from the group consisting of hydrogen, a hydroxyl group, a halogen, a hydrocarbon moiety, and a substituted hydrocarbon moiety; and Z individually may be omitted entirely, but when present is selected from the group consisting of hydrogen, a halogen, a hydrocarbon moiety, and a substituted hydrocarbon moiety.

It will be recognized and appreciated that Formulas I and II respectively are presented using conventional chemical structure, format, and notations for amino acids and peptide organization as those found in Albert L. Lehninger's text, *Biochemistry, The Molecular Basis of Cell Structure And Function*, 2nd edition, Worth Publishers, Inc., 1977—the text of which is expressly incorporated by reference herein. Moreover, Formulas I and II respectively by their definitions intend that all presently known and future embodiments of naturally occurring and non-naturally generated substances—which are by chemical formulation and structure one of those cyclic decapeptides forming the class of antamanides and antamanide analogues (including all substituted and derivatized forms)—lie within the scope of the present invention. However, the more desirable embodiments are those described and synthesized by U.S. Pat. Nos. 3,705,887, 3,793,304, and 3,211,716—the texts of each being expressly incorporated by reference herein. These issued patents not only provide the best embodiments of naturally occurring and non-naturally generated antamanides; but also provide complete and detailed procedures and techniques for synthesizing and purifying antamanides and antamanide analogues for use in the present methodologies.

Accordingly, a most preferred embodiment use for treatment of interleukin-mediated edema is the naturally occurring antamanide defined by Formula III, which is:

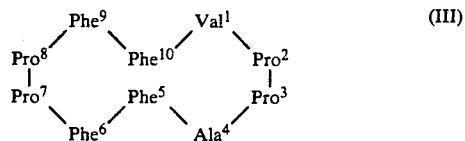

(III)

Other preferred embodiments of non-naturally occurring antamanides believed useful for treating interleukin-mediated edemas is given by Formulas IVA–IVD:

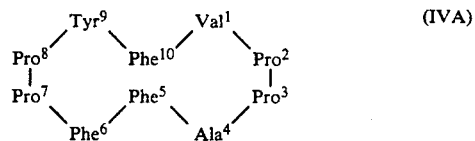

(IVA)

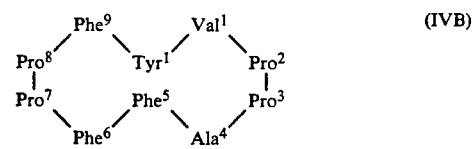

(IVB)

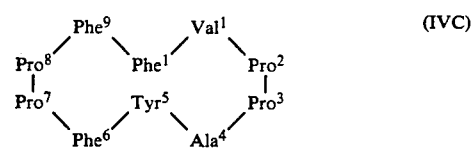

(IVC)

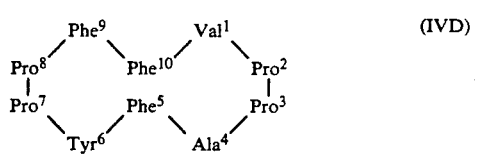

(IVD)

Within the various embodiments encompassed by Formulas I-IV inclusively, it will be recognized that the amino acids at the No. 1 position, typically L-valine, and at the No. 4 position, typically alanine, may be substituted by other amino acids. At a minimum, these other amino acids are acyclic—and by definition do not contain any ring structure within their composition. In addition, it is preferable that these amino acids also do not comprise a secondary nitrogen atom, a secondary carboxylic acid group, nor any sulfur atom. The preferred choices of "X" include L-leucine and L-isoleucine in addition to L-valine and L-alanine.

In comparison, the suitable amino acids at position Nos. 5, 6, 9, and 10 within the cyclic decapeptide structure each require the presence of a cyclic ring component. Preferred are hydrophobic side-chains such as a benzene ring of 6 carbon atoms. However, it is expected that other ring configurations ranging from 3–6 carbon atoms which are alternatively saturated or unsaturated in varying degree will also be useful. Accordingly, the broadest definition provided by Formula I requires the "W" positions only to be filled by an amino acid having at least one ring structure comprised of not more than 6 carbon atoms.

The given recitations of "Y" and "Z" identify commonly available chemical substitutions and derivatized forms for the general membership of the class comprising antamanides and antamanide analogues. The various substitutions and additions to the cyclic decapeptide structure are performed using commonly known syntheses and chemical reaction techniques. All of the embodiments of "Y" and "Z" are matters of personal choice and convenience well within the skills of the ordinary practitioners in this field. The preferred methods for synthesizing the cyclic decapeptides comprising Formulas I-IV inclusive are those conventionally known and described in detail within U.S. Pat. Nos. 3,705,887, 3,793,304, and 3,211,716 respectively. The synthesis is preferably performed using acyclic decapeptides which are then cyclized into the overall cyclic form using conventional methods in peptide synthesis. In general, the cyclization from linear into cyclic form may take place at any position using the acyclic precursor peptide unit where an amino group and a carboxyl group are available for reaction. In the case of the amino acid proline, the imino group (HN=) may be present at the end of the chain instead of an amino group ($H_2N-$).

As noted in the cited patents, two processes are mainly involved, both of which however are suitable for general application and synthesis. In the first process, one end of the acyclic chain, preferably the carboxyl group, is applied in an activated form, while the amino reactive group has already been reversibly protected, or if this is not the case, must initially be protected. The amino protective group is then selectively split off in such a way that the amino group thus liberated is protected simultaneously by proteination. The deproteination of the reactive amino group by bases in highly dilute solution leads to cyclization.

The second general process employs a peptide zwitterion, the amino group of which is already present in proteinated condition. By activation of the carboxyl group and the addition of a base in diluted solution, or by addition of a dehydrating agent to the peptide zwitterion, the cyclic end-product is also obtained in one step. Both of the general cyclization methods are performed in relatively great dilutions in order to suppress di- and poly-condensations.

In comparison, phallotoxins and phallotoxin analogues are bicyclic heptapeptides and are most broadly defined by Formula V and Table 1 below.

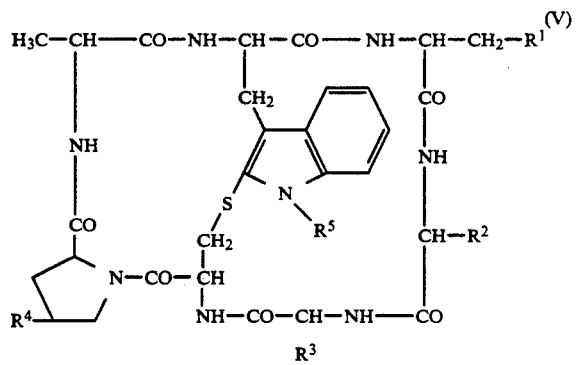

TABLE I

| PHALLOTOXIN | SIDE CHAINS |
|---|---|
| A. Natural Phallotoxins | |
| Ia Phalloidin | $R^1$ = C(CH$_3$)OH—CH$_2$OH |
| | $R_3$ = CH$_3$ |
| | $R_4$ = C(H)OH—CH$_3$(threo) |
| | $R^4$ = OH(allo) $R^5$ = H |
| Ib Phalloin | $R^1$ = C(CH$_3$)OH—CH$_3$ |
| | $R^2$ = $R^5$ as in Ia |
| Ic Phallisin | $R^1$ = C(OH) (CH$_2$OH)$_2$ |
| | $R^2$ = $R^5$ as in Ia |
| Id Phallacidin | $R^1$ = C(CH$_3$)OH—CH$_2$OH |
| | $R^2$ = CH(CH$_3$)$_2$ |
| | $R^3$ = C(H)OH—CO$_2$H(erythro) |
| | $R^4$ = OH(allo) $R_5$ = H |
| B. Chemically Modified Phallotoxins | |
| Ie Ketophalloidin | $R^1$ = CO—CH$_3$ |
| | $R^2$ = $R^6$ as in Ia |
| If Norphalloin | $R^1$ = CH$_2$—CH$_3$ |
| | $R^2$ = $R^5$ as in Ia |
| Ig Monoacetylphalloidin | $R^1$ = C(CH$_3$)OH—CH$_2$OAc |
| | $R^2$ = $R^5$ as in Ia |
| Ih Monotosylphalloidin | $R^1$ = C(CH$_3$)OH—CH$_2$-Otos |
| | $R^2$ = $R^5$ as in Ia |
| Ii Diacetylphalloidin I | $R^1$ = as Ig |
| | $R^2$ = as in Ia |
| | $R^3$ = C(H) OAc—CH$_3$ |
| | $R^4$ = $R_5$ as in Ia |
| Ij Diacetylphalloidin II | $R^1$ = as in Ig |
| | $R^2$ = $R^3$ as in Ia |
| | $R^4$ = OAc(allo) $R^5$ = H |
| Ik Triacetylphalloidin | $R^1$ = $R^3$ as in Ii |
| | $R^4$ = $R^5$ as in Ig |
| Il Ditosylphalloidin | $R^1$ = as in Ih, second tosyl either in $R^3$ or $R^4$ of Ih |
| Im Tritosylphalloidin | $R^1$ = as in Ih, 2nd and 3rd tosyl in $R^3$ and $R^4$ of Ih |
| In Tribomophalloidin | 3 Br instead of OTos in Im (probably Walden inversion in $R^3$ and $R^4$) |
| Io N-Methylphalloidin | $R^5$ = CH$_3$ in Ia |
| Ip N-Ethylphalloidin | $R^5$ = C$_2$H$_5$ in Ia |
| Iq N-Propylphalloidin | $R^5$ = n-C$_3$H$_7$ in Ia |
| Ir N-Pentylphalloidin | $R^5$ = n-C$_5$H$_{11}$ in Ia |
| Is N-tert. Butylphalloidin | $R^5$ = t-C$_4$H$_9$ in Ia |
| It Carbamoylmethylphalloidin | $R^5$ = CH$_2$CONH$_2$ in Ia |
| C. Ring Open Products | |
| Iu Dothiophalloidin | in $P^6$ of Ia S removed, substituted by 2 H at bridgebends |
| Iv Seco-15-Phalloidin | Peptide bond in $P^7$ of a Ia hydrolytically split |
| Iw Seco-18-Phallotoxin | $R^1$-$R^5$ as in If, but instead of peptide bond at $P^8$ COOiBut at N and NH$_2$ at Co |
| Ix Bis-seco-15,18-phallotoxin | Open at $P^8$ and between threonine and cysteine |

Source:
Faulstich, H. and T. Wieland, Eur. J. Biochem. 22: 79–86 (1971).

The preferred embodiments of phallotoxins as a class are the naturally occurring compounds isolated from *Amanita phalloides* and include the bicyclic heptapeptides phalloidin, phallacidin, phalloin, phallisin, prophalloin, phallisacin, and phallacin. The composition and individual methods of preparation for each naturally occurring member are conventionally known and published in the scientific literature [Wieland et al., Pharmacol. Rev. 11:87–107 (1959); Wieland et al., Crit. Rev. Biochem. 5:185–260 (1978)]. Methods for generating the chemically synthesized phallotoxin analogues of Formula V and Table I are conventionally known.

Each member within the class phallotoxins is believed to be individually active and effective in varying degree; and each is expected to act directly on the vasculature of the cell and not via an indirect metabolic cascade for control of interleukin-mediated edemas. Within the class, phalloidin is presently considered to be the most effective composition; and for this reason, the remainder of the detailed description will focus upon and utilize phalloidin alone or in combination with antamanide as the best representatives of their respective classes. It will be expressly understood, however, that any of the other members within the class consisting of antamanide, antamanide analogues, phallotoxins, and phallotoxin analogues may be similarly employed and used effectively as needed or desired.

In-vivo treatment with antamanides, or antamanide analogues, or phallotoxins, or phallotoxin analogues is intended to be a general methodology for treatment of interleukin-mediated edemas in living subjects, particularly humans. The scope of effective treatment using the present invention includes: both prophylactic and therapeutic applications; treatment of localized or systemic interleukin caused edemas; and treatment given independently or in combination with other medical and/or surgical modalities. The present invention is useful and effective with any one or any combination of these parameters.

Any of the antamanides, or antamanide analogues, or phallotoxins, or phallotoxin analogues encompassed by Formulas I-V respectively may be administered to the living subject by one of two different routes: topically by direct application to the skin of the subject; and parenterally by injection or perfusion. If the substance of choice is to be applied topically, the heptapeptide or decapeptide composition can be admixed in a pharmacologically inert topical carrier such as a gel, an ointment, a lotion, or a cream; and includes such carriers as water, glycerol, alcohol, propylene glycol, fatty alcohols, triglycerides, fatty acid esters, or mineral oils. Other possible topical carriers include liquid petrolatum, isopropylpalmitate, polyethylene glycol, ethanol, polyoxyethylene monolourate in water, sodium lauryl sulfate in water, and the like. Other materials such as anti-oxidantts, humectants, viscosity stabilizers, and the like may also be added as desired or necessary. In addition, it is expected (and in many instances desirable) that the substance of choice be disposed within devices placed upon, in, or under the skin; such devices include patches and implants which release the active material into the skin or body either by diffusion or by an active release mechanism.

Alternatively, if the antamanide, or antamanide analogue, or phallotoxin, or phallotoxin analogue is to be given parenterally, it is expected that the composition will be prepared in sterile form; in multiple or single dose formats; and dispersed in a fluid carrier such as sterile physiological saline or 5% dextrose solutions commonly used with injectables.

In general, the concentration of the chosen antamanide or antamanide analogue (employed independently or combined with other substances) which may be effectively employed for prophylactic and/or therapeutic treatment of living subjects is expected to be: for topical applications, a range concentration from about 1-10 micrograms (hereinafter "ug") per gram of topical carrier. For intravenous, perfusion and other parenteral administration, a concentration range of from about 1.0 micromolar-0.1 micromolar per $L^{-1}$ of blood.

Similarly, the concentration of phallotoxin or phallotoxin analogue (employed independently or combined with other substances) which may be effectively employed for prophylactic and/or therapeutic treatment of living subjects is expected to be: for topical applications, a range concentration from about 1-10 micrograms (hereinafter "ug") per gram of topical carrier. For intravenous, perfusion and other parenteral administration, a concentration range of from about 1.0 micromolar-0.1 micromolar per $L^{-1}$ of blood.

In addition, when the chosen phallotoxin heptapeptide or antamanide decapeptide composition is employed for prophylactic or therapeutic treatment of an interleukin-induced or involved edema which is a coincidental characteristic of an inflammatory reaction, it is most desirable that the heptapeptide or decapeptide be administered in admixture with a variety of anti-inflammatory compounds. These include: aspirin, ibuprofen, thromboxane synthase inhibitors; receptor antagonists for the thromboxanes; prostanoid metabolic drugs; steroids; and superoxide and free radical scavengers.

A major advantage of the present invention is its ability to prophylactically or therapeutically treat interleukin-mediated edema, either at localized sites or systemically. To empirically demonstrate the clinical circumstances in which the present methodology can be beneficially employed, a single cyclic decapeptide defined by Formula III above was empirically evaluated. The embodiment is the naturally occurring form produced and isolatable from the *Amanita phalloides* fungus. Its amino acid sequence comprises L-valine at the No. 1 position; L-alanine at the No. 4 position; L-phenylalanine at position Nos. 5, 6, 9, and 10; and L-proline at position Nos. 2, 3, 7, and 8. For ease of description annd for clarity of presenntation, this embodiment will be termed "antamanide." Similarly, a single bicyclic heptapeptide defined by Formula V was empirically tested. This embodiment was phalloidin which also is a naturally occurring form isolatable from the same fungus.

EXPERIMENTAL SERIES

Protocol: In-Vivo

1. Assay Models: Vascular leak syndrome is induced rapidly in adult, male rats (500 g) by a continuous infusion for 1 h of $10^6$ units of IL-2 (n=36). Five hours later the animals are killed and edema is quantitated by measuring wet to dry (W/D) ratios for the lungs, kidneys, liver, heart, and spleen.

2. Controls: Animals are pretreated with 0.5 ml saline for 30 min. prior to the IL-2 infusion (n=28).

3. Experimental Animals: Each animal is pretreated with either Phallin A (antamanide) or Phallin B (phalloidin), 20 ug/0.5 ml saline as a single bolus 30 min. prior to the infusion of IL-2 (n=24). Each animal then receives at 30 min. intervals a booster injection of 20 ug of Phallin A or Phallin B for the duration (6 h) of the experiments.

4. Protein Analysis: Samples obtained by bronchoalveolar lavage are quantitated for protein concentration as another means of determining the relative loss of barrier integrity in the experimental animals compared to controls.

Results

Spleen Wet to Dry Ratio: As shown by FIG. 1, administration of phalloidin (1 uM) alone, antamanide (1 uM) alone, or $10^5$ U/ml Interleukin-2 alone did not produce any significant splenic edema. $10^6$ U/ml IL-2 also failed to induce splenic edema, which remained unmodified by antamanide or phalloidin.

Figure 2:
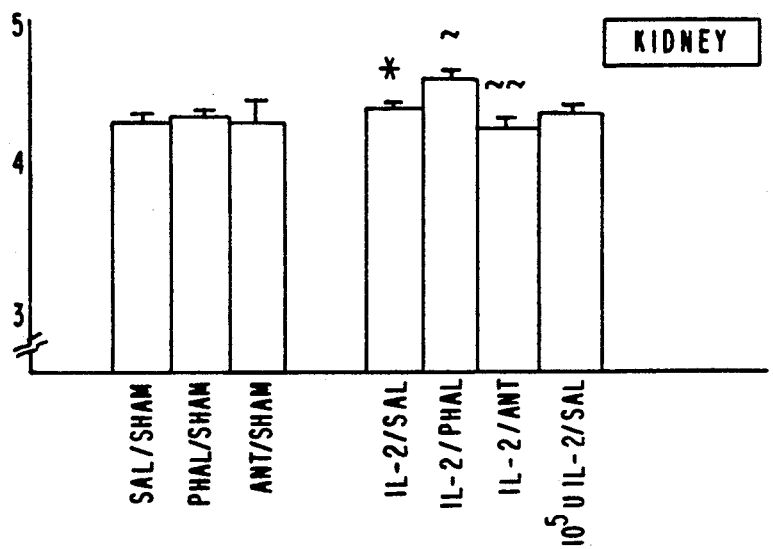
FIG. 2 is a graph illustrating the kidney wet to dry weight ratios after in-vivo administration of Interleukin-2, phalloidin, and antamanide alone and in combination.

Kidney Wet to Dry Ratio: As seen in FIG. 2, administration of phalloidin (1 uM) alone, antamanide (1 uM) alone, or $10^5$ U/l Interleukin-2 alone did not produce any significant renal edema. Administration of $10^6$ U/ml IL-2 produced a significant increase in edema, which was significantly ($p<0.05$) worsened by phalloidin (1 uM). This edema was signnificantly improved ($p<0.05$) by antamanide (1 uM).

Figure 3:
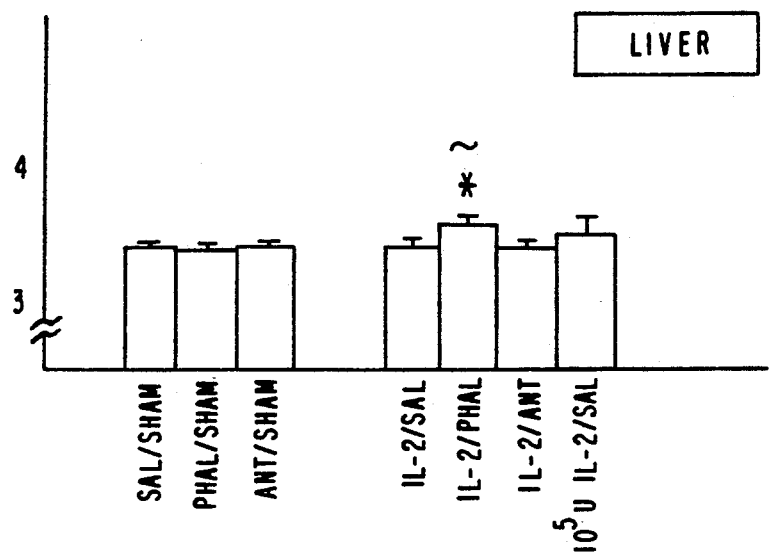
FIG. 3 is a graph illustrating the liver wet to dry weight ratios after in-vivo administration of Interleukin-2, phalloidin, and antamanide alone and in combination.

Liver Wet to Dry Ratio: As illustrated by FIG. 3, administration of phalloidin (1 uM) alone, antamanide (1 uM) alone, or $10^5$ U/ml Interleukin-2 alone did not produce any significant hepatic edema. Administration of $10^6$ U/ml IL-2 produced no significant increase in edema. IL-2 plus phalloidin (1 uM) produced significant ($p<0.05$) edema. No significant change in wet/dry weight ratio was seen in an antamanide/IL-2 co-treatment.

Figure 4:
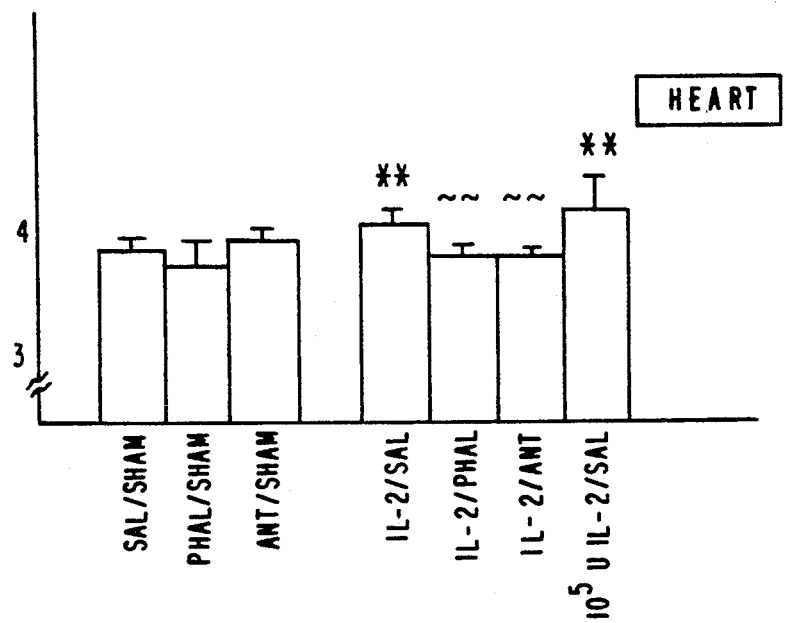
FIG. 4 is a graph illustrating the heart wet to dry weight ratios after in-vivo administration of Interleukin-2, phalloidin, and antamanide alone and in combination.

Heart Wet to Dry Weight Ratio: As provided by FIG. 4, administration of phalloidin (1 uM) alone, antamanide (1 uM) alone, or $10^5$ U/ml Interleukin-2 alone did not produce any significant cardiac edema. Administration of $10^6$ U/mml IL-2 produced a significant ($p<0.01$) increase in edema, which was significantly reduced by either phalloidin (1 uM) ($p<0.01$) co-treatment, or antamanide co-treatment (1 uM) ($p<0.01$).

Figure 5:
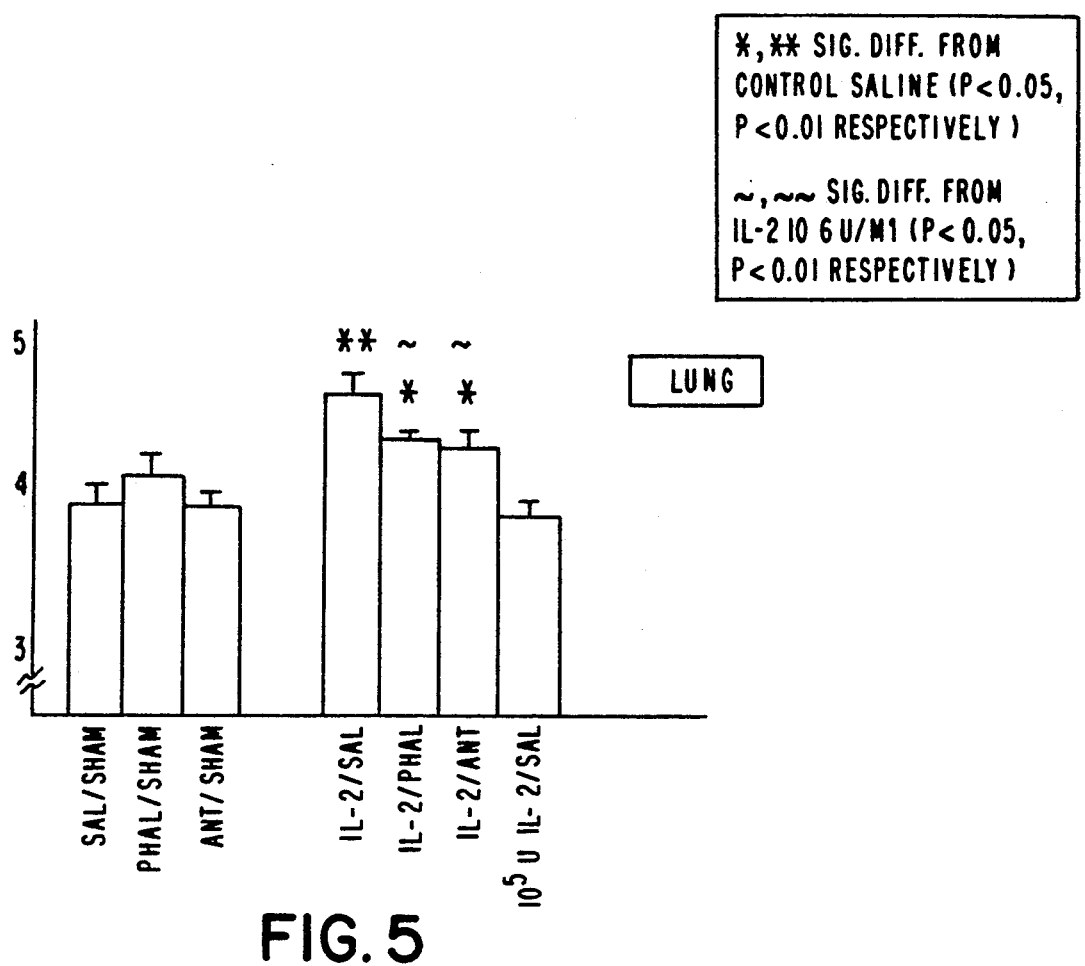
FIG. 5 is a graph illustrating the lung wet to dry weight ratios after in-vivo administration of Interleukin-2, phalloidin, and antamanide alone and in combination.

Lung Wet to Dry Weight Ratio: As presented by FIG. 5, administration of phalloidin (1 uM) alone, antamanide (1 uM) alone, or $10^5$ U/ml Interleukin-2 alone did not produce any significant pulmonary edema. Administration of $10^6$ U/ml IL-2 produced a significant ($p<0.01$) increase in edema, which was significantly reduced by either phalloidin (1 uM) ($p<0.05$) co-treatment, or antamanide co-treatment (1 uM) ($p<0.05$).

Figure 6:
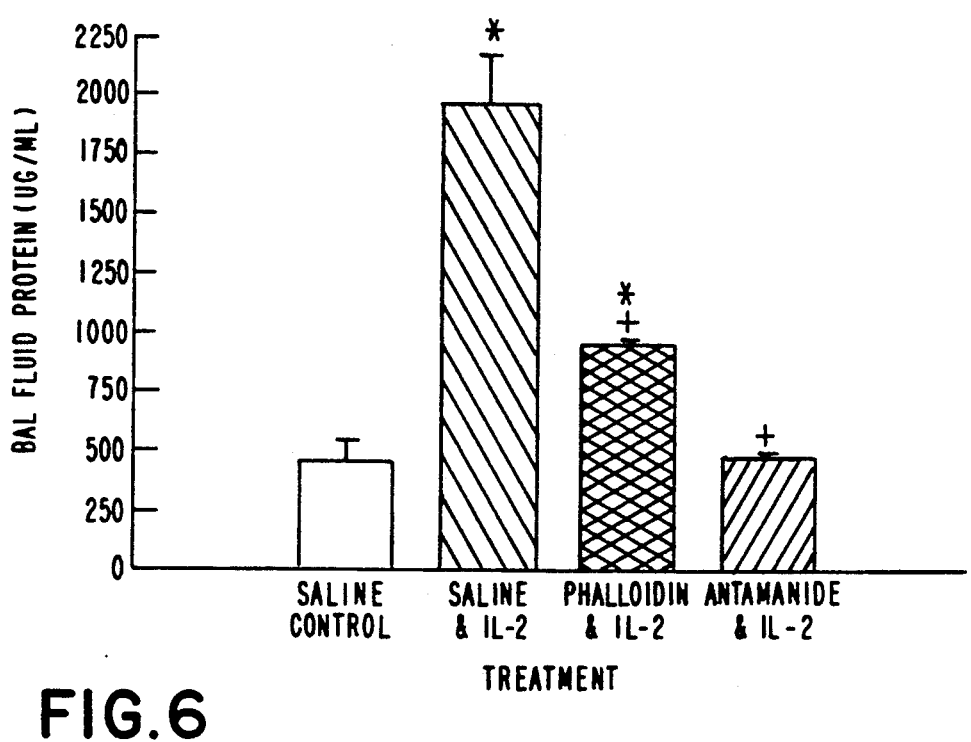
FIG. 6 is a graph illustrating the decrease in bronchoalveolar lavage fluid protein after in-vivo administration of Interleukin-2, phalloidin, and Interleukin-2, and antamanide and Interleukin-2 respectively.

Protein Concentrations of Alveolar Fluid: As presented by FIG. 6, the administration of phalloidin (1 uM) and $10^6$ U/ml Interleukin-2 in admixture or the administration of antamanide (1 uM) and $10^6$ U/ml Interleukin-2 in combination drastically reduced the accumulation and concentration of protein in bronchoalveolar lavage fluid when compared to the effects of administering $10^6$ U/ml Interleukin-2 alone. The degree of difference is most drastic when the effect of administering saline alone are taken into account. Clearly, the phallotoxin markedly reduces the protein concentration; while the antamanide greatly decreases and almost neutralizes the vascular consequennces of IL-2 administration completely.

Overall, therefore, IL-2 ($10^6$ units) produces edema in the lungs (FIG. 5), heart (FIG. 4), and kidney (FIG. 2) relative to control values. No significant changes over controls are found in the spleen (FIG. 1) and liver (FIG. 3).

Treatment with Phallin B decreases IL-2 induced edema in the lung and heart; however, Phallin B apparently produces edema in the kidney and the liver. In contrast, treatment with Phallin A prevented IL-2 induced edema in the lungs, heart, and kidney; moreover, the liver and spleen appear unaffected.

The empirical data reported demonstrate that both phalloidin (1 uM) and antamannide (1 uM) can protect against dosage-dependent edemogenic effects of Interleukin-2 in the heart and in the lung. Antamanide, unlike phalloidin, always protected against Interleukin-2 mediated edemas in at least some organs and tissues; phalloidin, however, can improve or worsen IL-2 induced edema depending upon the organ examined. These data indicate that antamanide and phalloidin individually can be employed as agent(s) to reduce interleukin-mediated edemas produced by iatrogenic therapies.

The present invention is not to be limited in scope nor restricted in form except by the claims appended hereto.

What we claim is:

1. A method for therapeutically treating an interleukin 2-mediated edema in at least one organ selected from the group consisting of the lung, heart and kidney, said organ edema resulting from an interleukin 2-mediated breach of the microvascular barrier of said organ in a living subject, said method comprising the step of:

administering an effective amount of an antamanide compound to the living subject after occurrence of the interleukin 2-mediated edema, said antamanide compound having the formula

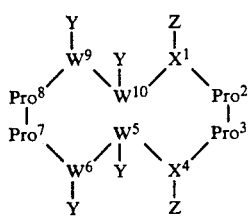

wherein W individually is an amino acid having at least one ring structure comprised of not more than 6 carbon atoms;

X individually is an acyclic amino acid comprised of 3-9 carbon atoms;

Y individually is omittable entirely but when present is selected from the group consisting of hydrogen, a hydroxyl group, a halogen, and a hydrocarbon moiety; and Z individually is omittable entirely but when present is selected from the group consisting of hydrogen, a halogen, and a hydrocarbon moiety.

2. A method for prophylactically treating an interleukin 2-mediated edema in at least one organ selected from the group consisting of the lung, heart and kidney, said organ edema resulting from an interleukin 2-mediated breach of the microvascular barrier of said organ in a living subject, said method comprising the step of:

administering an effective amount of an antamanide compound to the living subject prior to occurrence of the interleukin 2-mediated edema, said antamanide compound having the formula

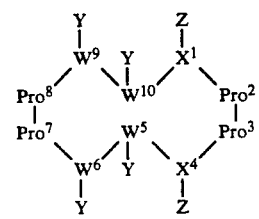

wherein W individually is an amino acid having at least one ring structure comprised of not more than 6 carbon atoms;

X individually is an acyclic amino acid comprised of 3-9 carbon atoms;

Y individually is omittable entirely but when present is selected from the group consisting of hydrogen, a hydroxyl group, a halogen, and a hydrocarbon moiety; and Z individually is omittable entirely but when present is selected from the group consisting of hydrogen, a halogen, and a hydrocarbon moiety.

3. A method for therapeutically treating an interleukin 2-mediated edema in at least one organ selected from the group consisting of the lung, heart and kidney, said organ edema resulting from an interleukin 2-mediated breach of the microvascular barrier of said organ in a living subject, said method comprising the step of:

administering an effective amount of an antamanide compound to the living subject after occurrence of the interleukin 2-mediated edema, said antamanide compound having the formula

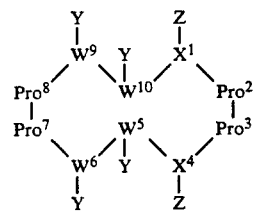

wherein W individually is an amino acid having a benzene ring in its structure;

X individually is an amino acid selected from the group consisting of valine, alanine, leucine, and isoleucine;

Y individually is omittable entirely but when present is selected from the group consisting of hydrogen, a hydroxyl group, a halogen, and a hydrocarbon moiety; and Z individually is omittable entirely but when present is selected from the group consisting of hydrogen, a halogen, and a hydrocarbon moiety.

4. A method for prophylactically treating an interleukin 2-mediated edema in at least one organ selected from the group consisting of the lung, heart and kidney, said organ edema resulting from an interleukin 2-mediated breach of the microvascular barrier of said organ in a living subject, said method comprising the step of:

administering an effective amount of an antamanide compound to the living subject prior to occurrence of the interleukin 2-mediated edema, said antamanide compound having the formula

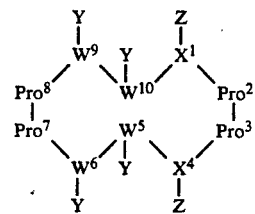

wherein W individually is an amino acid having a benzene ring in its structure;

X individually is an amino acid selected from the group consisting of valine, alanine, leucine, and isoleucine;

Y individually is omittable entirely but when present is selected from the group consisting of hydrogen, a hydroxyl group, a halogen, and a hydrocarbon moiety; and Z individually is omittable entirely but when present is selected from the group consisting of hydrogen, a halogen, and a hydrocarbon moiety.

5. The method as recited in claim 1, 2, 3, or 4 wherein said administration is parenteral.

6. The method as recited in claim 1, 2, 3, or 4 wherein said antamanide compound is naturally occurring.

7. The method as recited in claim 1, 2, 3, or 4 wherein said antamanide compound is synthetically generated.

* * * * *